(12) United States Patent
Dampney et al.

(10) Patent No.: US 6,818,007 B1
(45) Date of Patent: Nov. 16, 2004

(54) TOOL AND AN EFFECTOR

(75) Inventors: Ian Trevor Dampney, Pinner (GB); John Ewant Alfred Wickham, Pinner (GB)

(73) Assignee: Syclix Limited, Pinner (GB)

( * ) Notice: Subject to any disclaimer, the term of this patent is extended or adjusted under 35 U.S.C. 154(b) by 0 days.

(21) Appl. No.: 10/088,449

(22) PCT Filed: Sep. 15, 2000

(86) PCT No.: PCT/GB00/03565

§ 371 (c)(1),
(2), (4) Date: Jun. 11, 2002

(87) PCT Pub. No.: WO01/19261

PCT Pub. Date: Mar. 22, 2001

(30) Foreign Application Priority Data

Sep. 16, 1999 (GB) ................................ 9921946

(51) Int. Cl.[7] ............................................. A61B 17/28
(52) U.S. Cl. .................... 606/205; 606/207; 606/208
(58) Field of Search ................... 606/207, 206, 606/208, 205, 147, 170, 167, 174, 188

(56) References Cited

U.S. PATENT DOCUMENTS

| 5,052,402 | A | | 10/1991 | Bencini et al. |
| 5,147,357 | A | | 9/1992 | Rose et al. |
| 5,219,357 | A | | 6/1993 | Honkanen et al. |
| 5,263,967 | A | | 11/1993 | Lyons, III et al. |
| 5,290,309 | A | * | 3/1994 | Kothe ......................... 606/207 |
| 5,389,104 | A | | 2/1995 | Hahnen et al. |
| 5,476,479 | A | | 12/1995 | Green et al. |
| 5,590,570 | A | * | 1/1997 | LeMaire et al. .......... 74/579 R |
| 5,695,521 | A | * | 12/1997 | Anderhub .................... 606/205 |
| 5,700,275 | A | * | 12/1997 | Bell et al. .................... 606/208 |
| 5,904,702 | A | * | 5/1999 | Ek et al. ...................... 606/206 |
| 5,906,630 | A | | 5/1999 | Anderhub et al. |
| 5,964,779 | A | * | 10/1999 | Mayenberger et al. ...... 606/205 |
| 6,010,523 | A | * | 1/2000 | Sabin et al. ................. 606/205 |
| 6,015,426 | A | | 1/2000 | Griffiths |
| 6,053,933 | A | * | 4/2000 | Balazs et al. ............... 606/205 |
| 6,086,606 | A | * | 7/2000 | Knodel et al. .............. 606/208 |
| 6,228,083 | B1 | * | 5/2001 | Lands et al. ................... 606/50 |
| 6,582,451 | B1 | * | 6/2003 | Marucci et al. ............. 606/207 |

FOREIGN PATENT DOCUMENTS

| DE | 4444025 A1 | 6/1996 | |
| EP | 0589454 A2 | 3/1994 | |
| EP | 0623316 A1 * | 11/1994 | ................. 606/207 |
| WO | WO 93/12722 A1 | 7/1993 | |
| WO | WO 95/19145 A | 7/1995 | |
| WO | WO 96/02193 A | 2/1996 | |

* cited by examiner

Primary Examiner—Pedro Philogene
(74) Attorney, Agent, or Firm—David S. Kashman; Gottlieb, Rackman & Reisman

(57) ABSTRACT

An effector comprises a pair of opposing jaws directly mounted on a keeper so that the jaws are pivotable about the keeper. The jaws are connected to an actuating member within the keeper, so that translational movement of the actuating member causes the jaws between an open and closed position.

20 Claims, 2 Drawing Sheets

TOOL AND AN EFFECTOR

BACKGROUND OF THE INVENTION

The present invention relates to an effector and to a tool, and particularly, but not exclusively to a surgical tool and an effector therefor.

A known form of surgical tool has an effector mounted at the end of a shaft. The effector has two jaws and is actuated by an actuating member in the shaft. The jaws are pivotally attached to one another scissor fashion by means of a pin joint. The pivotal end of each jaw is attached to a respective ink by a further pin joint. The links attached to the jaws are attached to one another and to the actuating member in the shaft by means of a still further pin joint. Translational movement of the actuating member in the shaft causes the links to move in a scissor-like manner so that the jaws open and close. When the jaws are closed, the jaws, links and actuating member are aligned, axially of the shaft. However, when the jaws are fully open the links and the pivotal ends of the jaws project laterally beyond the diameter of the shaft.

This lateral projection of the links and jaws beyond the diameter of the shaft is undesirable since the tissue of the patient may be caught in the links and jaws of the tool. Furthermore, the pins of the pin joints are very small, so that it is difficult to install the pins securely. The small size of the pins also means that they are very prone to fracture. Again, such fractures are obviously undesirable since they result in the introduction of foreign material into the patient. The mechanical advantage of the tool also varies according to the position of the jaws. As the jaws approach the closed position, the mechanical advantage of the system is greatly reduced in comparison with the mechanical advantage when the jaws are in the fully open position.

SUMMARY OF THE INVENTION

An object of the present invention is to provide a tool in which the above disadvantages are overcome.

The invention provides an effector as claimed in claim 1 and a tool as claimed in claim 17.

An embodiment of the invention will now be described with reference to the drawings, in which:

DETAILED DESCRIPTION OF THE PREFERRED EMBODIMENTS

Figure 1:
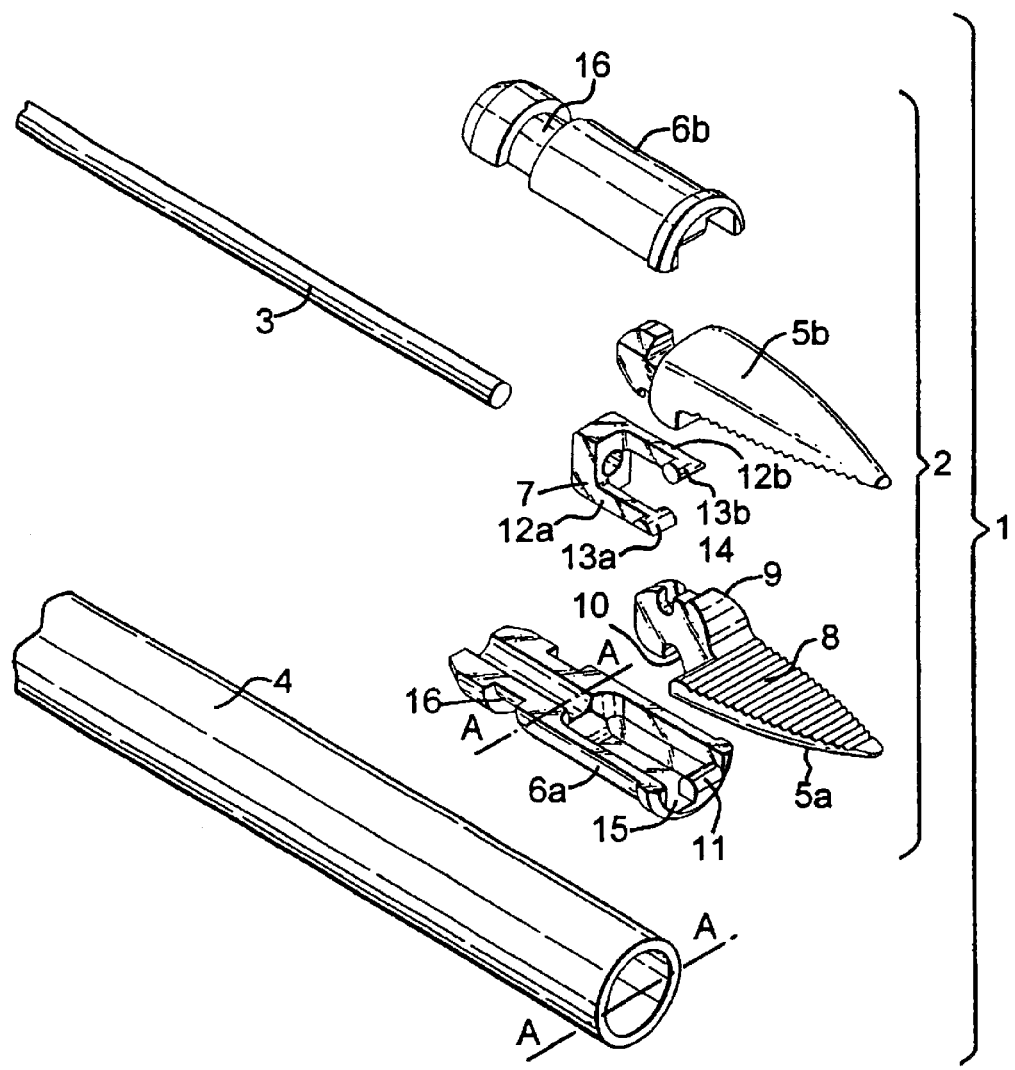
FIG. 1 shows an exploded perspective view of a tool in accordance with the invention.

In FIG. 1, a surgical tool 1 has an effector 2, a pull rod 3 and a tube 4. The effector 2 comprises a pair of jaws 5a, 5b, a keeper 6 and an actuating member 7. The keeper 6 is divided along a plane of separation of the jaws 5a, 5b A—A to form two identical keeper parts, 6a and 6b. The effector 2 is rotationally symmetrical about the plane of separation of the jaws A—A. Each jaw 5a, 5b is associated with a respective keeper part 6a or 6b. The jaw 5a has an operational portion 8 which is used to carry out surgical procedures and an actuating portion 9, where the movement of the jaw is controlled. The outer surface of the operational portion 8 of the jaw 5a is smooth, while the inner surface of the jaw 5a may be serrated or uneven. The lower surface of the actuating portion 9 has pivoting means in the form of a notch 10 engageable with pivoting means in the form of a corresponding rib 11 on the keeper part 6a so that the jaw 5a may be pivoted about the rib 11 on the keeper part 6a. The rib 11 is arranged on the inner surface of the keeper part 6a. The notch 10 and the rib 11 are arcuate to facilitate pivotal motion of the jaw 5a about the keeper part 6a.

The actuating member 7 has an arm 12a projecting from its lower end in the direction of translational movement of the actuating member 7 and an actuating arm 12b projecting from its upper end, also in the direction of translational movement of the actuating member 7. Projections 13a and 13b are located at the end of the respective arms 12a and 12b, so that the arms 12a and 12b are slidable within a recess (see below) in the keeper parts 6a and 6b respectively and the actuating member 7 may thus be located in the keeper parts 6a and 6b. The projections 13a and 13b also permit engagement of the respective jaws 5b and 5a, so that the actuating member 7 can actuate the jaws 5a and 5b.

The jaw 5a has actuating means, arranged on an opposite side of the plane of separation of the jaws A—A to the jaw pivoting means, in the form of a recess 14 on the upper surface of the actuating portion 9. The recess 14 is engageable with actuating means in the form of the projection 13b on the actuating member 7 so that the jaw 5a may be actuated by the actuating member 7. The recess 14 and the projection 13b are arcuate in cross-section to permit pivotal motion of the jaw 5a around about the projection 13b. The keeper part 6a has a recess 15 adjacent the rib 11 for clearance of the projection 13a on the arm 12a of the actuating member 7 in the keeper part 6a. When the actuating member 7 is inserted in the keeper part 6b, the projection 13b engages in the recess 14 so that the top surface of the projection 13b is flush with the top surface of the actuating portion 9.

The pull rod 3 is also attached to the actuating member 7 so that the pull rod 3 may actuate the actuating member 7. The actuating member 7 may have a threaded bore and the pull rod 3 may be threaded so that the pull rod 3 and actuating member 7 can be connected together by means of the interengaging threads. Alternatively, the actuating member 7 may be moulded around serrations adjacent the end of the pull rod 3.

Figure 2:
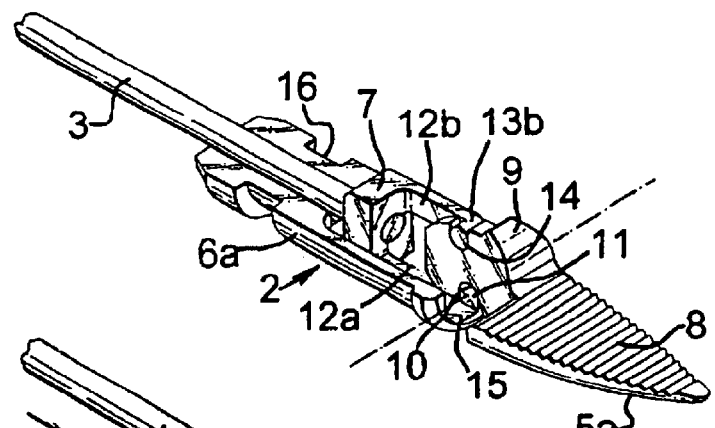
FIG. 2 shows a perspective view of one half of the effector of the tool of FIG. 1 in a closed position.
Figure 3:
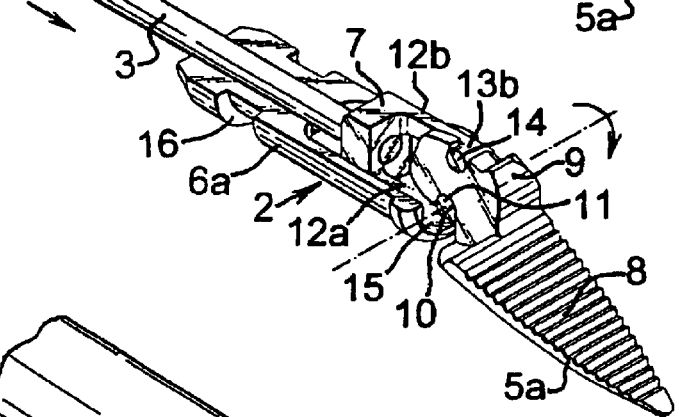
FIG. 3 shows a perspective view of one half of the effector of the tool of FIG. 1 in an open position.

FIGS. 2 and 3 show the actuating member 7 arranged in the keeper part 6a. The jaw 5a is also arranged on the keeper part 6a. The opposing jaw 5b (not shown) is arranged on the keeper part 6b in a similar manner. The actuating portion 9 of the jaw 5a is laterally offset from the actuating portion of the jaw 5b so that the actuating portions of the jaws 5a and 5b are located side by side in the keeper 6. When the jaws 5a, 5b, the actuating member 7 and the pull rod 3 are assembled in the keeper 6, the tube 4 is: slid over the keeper 6 to hold the assembly together and constrain radial movement of the components in the keeper 6. It is also desirable to constrain axial movement of the assembled components. The keeper parts 6a and 6b illustrated in the embodiment shown in FIGS. 1 to 3 have a groove 16 around their outer surface. When the tube 4 has been placed over the assembled components, the tube may be deformed around the groove 16 so that axial movement of the assembled components may be constrained. Alternatively, the outer surface of the keeper 6 may simply be bonded to the inner surface of the tube 4 to constrain axial movement of the keeper. It is also possible to include a resilient element on the keeper 6, for example, a pip or spring-loaded ball catch which engages a through hole in the tube 4, or vice versa, to constrain axial movement of the assembled components.

FIG. 2 shows one half of the assembly when the jaw 5a is in a closed position. In the closed position the pull rod 3 and actuating member 7 are in a retracted position. The jaw 5a rests on the rib 11 so that the jaw extends substantially parallel to the plane of separation of the jaws A—A. When the pull rod 3 is actuated so that it and the actuating member 7 move translationally within the keeper part 6a towards the jaw 5a, the projection 13b on the actuating member 7 pushes the jaw 5a, causing it to pivot about the rib 11 in a clockwise direction so that the jaw 5a opens (see FIG. 3). The pull rod 3 may be actuated by a variety of means, for example, by means of the actuator disclosed in UK patent application No. 9902647.8. It will be appreciated that the opposing jaw 5b (not shown) is pivoted in a similar manner in an anti-clockwise direction. The jaws 5a and 5b can be closed again by actuating the pull rod 3 and thus the actuating member 7 in the opposite direction so that they return to the retracted position.

Figure 4:
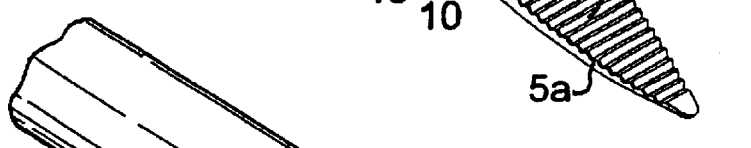
FIG. 4 shows the tool of FIG. 1 in the closed position.
Figure 5:
FIG. 5 shows the tool of FIG. 1 in the open position.

FIGS. 4 and 5 show respectively the position of the jaws 5 in the open and closed positions. It will be seen that even in the open position there are no components, with the exception of the jaws 5a and 5b themselves, protruding beyond the diameter of the tube 4, and the outer surface of the jaws is smooth. The risk of the tool catching on tissue of the patient is, therefore, minimised.

It will also be seen that the components are arranged in the tube 4 in such a way that it is very difficult for fluids and other matter to enter the tube 4. Although the tool of the present embodiment is designed to be disposable, it may also be used as a re-usable tool.

It is thus desirable for the fluids and other matter entering the tube 4 to be kept to a minimum to aid re-sterilisation.

The mechanical advantage of the tool is substantially constant over the range of movement of the jaws. The fact that the recess 14 and notch 10 are located on opposite sides of the plane of separation of the jaws means that the mechanical advantage of the tool is also maximised.

The components of the tool may be made of a variety of materials. For example, the tube may be made of stainless steel or titanium alloy, whereas the jaws may be made of plastics or metal.

Different jaws may be used for different applications. For example the jaws may be forceps, where gripping is required. However, the jaws may also be scissors or spreaders respectively where cutting and spreading is required. Although the tool has been described in the context of surgical use, it will be appreciated that the tool may be used in many other fields where delicate handling of materials is required, for example in the electronics industry, botany or entomology.

What is claimed is:

1. An effector comprising a pair of opposing jaws directly mounted on a keeper and pivotable thereabout, the jaws being connected to an actuating member within the keeper, so that translational movement of the actuating member causes the jaws to pivot between an open and closed position, wherein each jaw has pivoting means engageable with respective pivoting means on the keeper and actuating means engageable with corresponding actuating means on the actuating member, the jaw actuating means and the jaw pivoting means being arranged at opposite sides of a plane of separation of the jaws.

2. An effector as claimed in claim 1, wherein the pivoting means comprise corresponding notches and ribs.

3. An effector as claimed in claim 2, wherein the notches are arranged on the jaws and the corresponding ribs are arranged on the keeper.

4. An effector as claimed in claim 2 or claim 3, wherein the notches and ribs are arcuate.

5. An effector as claimed in claim 1, wherein the keeper comprises at least two parts, one part being associated with each jaw.

6. An effector as claimed in claim 1, wherein the actuating member is connectable with a pulling rod.

7. An effector as claimed in claim 6, wherein the actuating member is connectable with the pulling rod by means of interengaging threads.

8. An effector as claimed in claim 1, wherein the actuating means comprise corresponding projections and recesses.

9. An effector as claimed in claim 8, wherein the recesses are arranged in the jaws and the projections are arranged on the actuating member.

10. An effector as claimed in claim 8 or 9, wherein the projections and recesses are arcuate.

11. An effector as claimed in claim 1, wherein the jaws are forceps, scissors or spreaders.

12. An effector as claimed in claim 1, wherein the jaws are made of plastics or metal.

13. An effector as claimed in claim 1, wherein the effector is rotationally symmetrical about the plane of separation of the jaws.

14. A tool comprising the effector as claimed in claim 1, a pull rod connected to the actuating member, and a tube surrounding the effector and the pull rod.

15. A tool as claimed in claim 14, wherein the pull rod is moulded around the actuating member.

16. A tool as claimed in claim 14 or 15, wherein the keeper is held within the tube by deformation of the tube around the keeper so that axial movement of the effector within the tube is constrained.

17. A tool as claimed in claim 14 or 15, wherein the keeper is held within the tube by bonding so that axial movement of the effector within the tube is constrained.

18. A tool as claimed in claim 14 or 15, wherein the keeper has resilient projections or notches engageable with corresponding notches or resilient projections in the tube, so that axial movement of the effector within the tube is constrained.

19. A tool as claimed in claim 14, wherein the tool is disposable.

20. An effector as claimed in claim 1, wherein the keeper is divided along a plane of separation of the jaws to form two identical keeper parts.

* * * * *